United States Patent [19]
Brown et al.

[11] Patent Number: 5,460,263
[45] Date of Patent: Oct. 24, 1995

[54] RETAINER FOR A SUTURE REEL DISPENSER

[75] Inventors: David L. Brown, Wallingford; Stanley J. Malinowski, Guilford; Hans-Jürgen P. Sinn, Fairfield, all of Conn.

[73] Assignee: United States Surgical Corporation, Norwalk, Conn.

[21] Appl. No.: 174,752

[22] Filed: Dec. 29, 1993

Related U.S. Application Data

[63] Continuation of Ser. No. 772,690, Oct. 7, 1991, abandoned.

[51] Int. Cl.⁶ .................................................. A61B 17/06
[52] U.S. Cl. ........................................... 206/63.3; 206/380
[58] Field of Search ................................. 206/63.3, 491, 206/492, 227, 380, 438, 363

[56] References Cited

U.S. PATENT DOCUMENTS

| | | |
|---|---|---|
| 2,930,479 | 3/1960 | Lowe . |
| 3,062,372 | 11/1962 | Egler et al. . |
| 3,167,895 | 2/1965 | Egler et al. . |
| 3,206,018 | 9/1965 | Lewis et al. . |
| 3,231,215 | 1/1966 | Horine . |
| 3,280,971 | 10/1966 | Regan, Jr. . |
| 3,301,392 | 1/1967 | Regan, Jr. . |
| 3,301,393 | 1/1967 | Regan, Jr. et al. . |
| 3,376,973 | 4/1968 | Granowitz et al. . |
| 3,444,994 | 5/1969 | Kaepernik et al. . |
| 3,490,192 | 1/1970 | Regan, Jr. . |
| 3,545,608 | 12/1970 | Berger et al. . |
| 3,627,120 | 12/1971 | Bordeau . |
| 3,648,949 | 3/1972 | Berger et al. . |
| 3,749,238 | 7/1973 | Taylor . |
| 3,876,068 | 4/1975 | Sonnino . |
| 3,901,244 | 8/1975 | Schweizer . |
| 4,084,692 | 4/1978 | Bilweis . |
| 4,089,409 | 5/1978 | Cerwin ................................. 206/388 X |
| 4,120,395 | 10/1978 | Mandel et al. ........................ 206/63.3 |
| 4,135,623 | 1/1979 | Thyen . |
| 4,253,563 | 3/1981 | Komarnycky ........................... 206/63.3 |
| 4,258,843 | 3/1981 | Wymer . |
| 4,412,613 | 11/1983 | Kubas . |
| 4,413,727 | 11/1983 | Cerwin et al. ........................ 206/63.3 |
| 4,491,218 | 1/1985 | Aday .................................... 206/63.3 |
| 4,496,045 | 1/1985 | Ferguson et al. . |
| 4,533,041 | 8/1985 | Aday et al. ........................... 206/63.3 |
| 4,615,435 | 10/1986 | Alpern et al. ......................... 206/63.3 |
| 4,616,469 | 10/1986 | Skalleberg . |
| 4,700,833 | 10/1987 | Smith . |
| 4,714,191 | 12/1987 | Richardson . |
| 4,884,681 | 12/1989 | Roshdy et al. . |
| 4,934,523 | 6/1990 | Strom . |
| 5,131,534 | 7/1992 | Brown et al. . |

FOREIGN PATENT DOCUMENTS

| | | |
|---|---|---|
| 2014380 | 4/1970 | France . |
| 2358164 | 2/1978 | France . |
| 2700077 | 1/1977 | Germany . |
| 1081123 | 8/1967 | United Kingdom . |
| 2132987 | 7/1984 | United Kingdom . |

*Primary Examiner*—Jacob K. Ackun

[57] ABSTRACT

A retainer for a suture reel dispenser includes three panels interconnected to each other by partial double perforated lines. The retainer in a folded condition forms a pocket to receive the suture reel dispenser. One panel, namely, the reel panel includes at least one reel engaging tab which engages the receptacle of the reel dispenser to restrict movement of the reel dispenser relative to the retainer to thereby prevent accidental removal from the retainer.

25 Claims, 7 Drawing Sheets

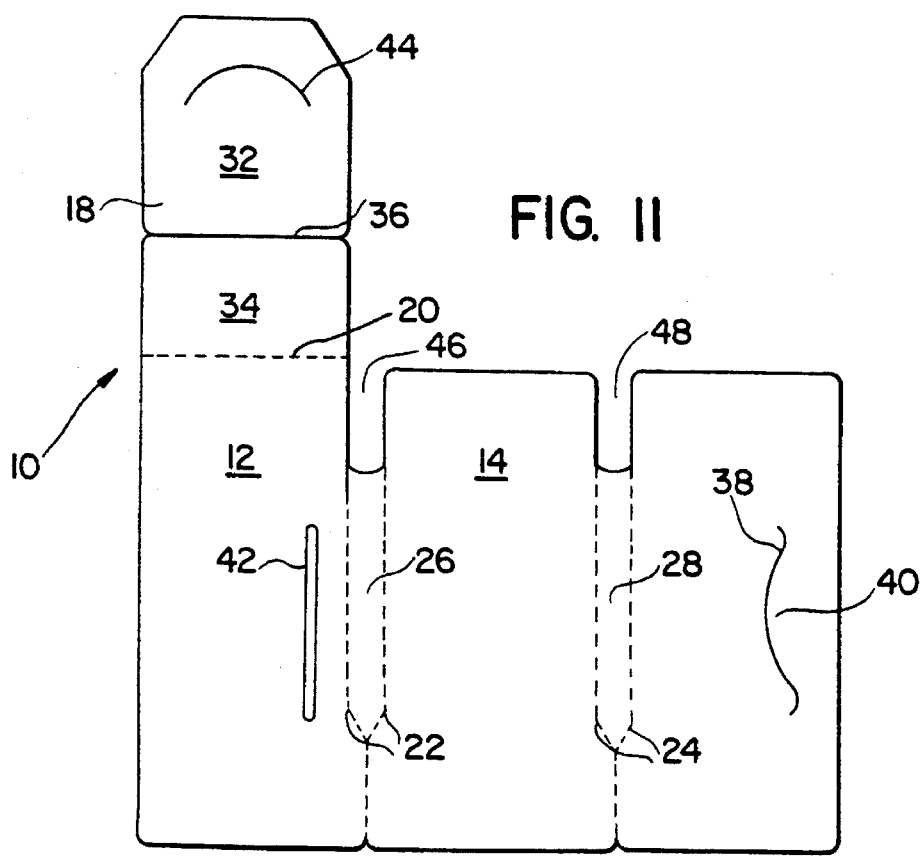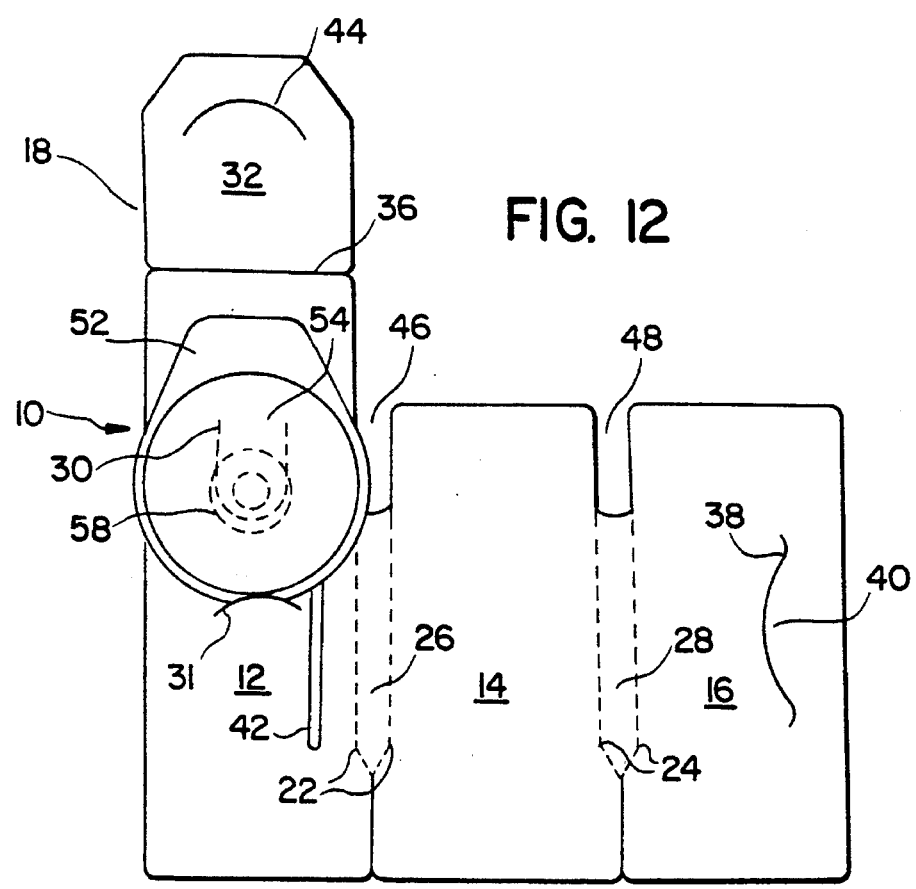

RETAINER FOR A SUTURE REEL DISPENSER

This is a continuation of application Ser. No. 07/772,690 filed on Oct. 7, 1991, and now abandoned.

BACKGROUND OF THE INVENTION

1. Field of the Invention

This invention relates to a surgical suture retainer and, more particularly, to a retainer for a suture reel dispenser.

2. Discussion of the Prior Art

Suture dispensers featuring a reel for storing a quantity of suture material have been developed to provide a desired length of suture material free of kinks or other irregularities, which can be used immediately without the need for straightening or similar preparative manipulation. In many of these known suture reel dispensers, a suture reel is rotatably seated within an outer casing and rotates to allow a desired length of suture to be played out.

Packaging of suture reel dispensers require that the reel dispensers be properly secured as well as being simply and quickly removable from their packages for use by the surgeon. U.S. Pat. No. 3,749,238 to Taylor describes a conventional reel dispenser retainer or package for a suture reel dispenser, which includes a molded-in plastic depth tray having a circular cavity for receiving a suture reel and a lid which is sealed about the periphery of the tray. U.S. Pat. Nos. 3,568,949 to Berger et al. and 3,545,608 to Berger et al. each describes a similar type package.

Although the molded-type tray retainers have proved to be adequate for storing and preserving the sterile qualities of a reel dispenser, there remains several significant problems with these retainers, foremost of which is that the reel dispenser packaged in a molded-type tray retainer is not easily passed to the surgeon during surgical procedures and is not in a position to be readily accessed by the surgeon. Furthermore, once the reel dispenser is removed from the tray retainer, the relative small size of the reel makes it difficult to handle.

Accordingly, the novel retainer of the present invention effectively stores a suture reel dispenser while also providing for ready accessibility of the dispenser during operating room procedures, and provides a means for easily handling a suture reel dispenser without risk of dropping the reel or unraveling the loaded suture material.

SUMMARY OF THE INVENTION

According to the present invention, a retainer for a suture reel dispenser comprises a first panel member serving as a reel panel, a second panel member foldably connected to the first panel member by a double perforated line and serving as a cover panel, a third panel member foldably connected to the second panel member by a double perforated line and serving as a back panel and an extension panel foldably connected to an upper edge of the first panel member. Each double perforated line forms a gusset between the interconnected panels. The extension panel is adapted to fold over the reel dispenser which is at least partially exposed at the upper edge of the first panel member. Means to secure the reel dispenser in the partially exposed position within the retainer is provided. The securement means may include a U-shaped reel tab formed in the first panel member, the reel tab being adapted to engage a component of the reel dispenser to prevent movement of the reel dispenser relative to the retainer. In an alternative embodiment, the securement means includes a pair of engaging tabs which are foldably connected to upper edges of the gussets. The engaging tabs are provided with notches which engage select components of the reel dispenser, and in this embodiment the second panel member serves as the reel panel.

Preferably, the extension panel defines an upper section and a lower section, the upper section being foldable along a perforated line over the lower section. A locking tab formed in the upper section engages an upper edge of the second panel member to secure the extension panel around the reel dispenser and to the retainer.

A crescent shaped opening may be provided in the first or third panel member with a corresponding slit provided in the remaining panel member. The opening and the slit cooperate with each other when the retainer is fully folded to provide a locking mechanism to secure the retainer in a closed position.

In a preferred embodiment, the retainer secures a suture reel dispenser of the type including a cylindrically shaped receptacle and an extension member connected to a section of the receptacle. The receptacle is adapted to rotatably receive a suture reel on one side, and includes a recess formed on the second side and may further include serrations formed on the outer peripheral surface. The retainer essentially is configured as previously described, with the first, second and third panel members folding onto each other to form a pocket to receive the reel dispenser.

The pocket of the retainer may be smaller than the diameter of the suture reel dispenser, and thus, as the reel dispenser is inserted into the pocket, the walls of the retainer pocket engage the circumferential walls of the reel dispenser, thereby limiting entry of the reel dispenser into the pocket and maintaining the dispenser in a partially exposed position above the upper edge of the first panel member. The gussets formed between the panel members expand slightly to accommodate the reel dispenser. In one embodiment, the reel tab formed in the first panel member engages the recess of the reel dispenser to limit upward movement of the dispenser relative to the retainer and to assist in securing the dispenser within the retainer. In a second embodiment, the engaging tabs are folded over the gusset, with the notches of the tabs engaging the serrations formed on the peripheral surface of the dispenser to secure the dispenser within the retainer.

BRIEF DESCRIPTION OF THE DRAWINGS

The foregoing features of the present invention will become more readily apparent and may be understood by referring to the following detailed description of an illustrative embodiment of the suture reel dispenser retainer, taken in conjunction with the accompanying drawings, in which:

FIG. 11 is a plan view of a further alternate embodiment of the retainer of FIG. 1;

FIG. 12 is a plan view of a further alternate embodiment of the retainer of FIG. 1;

DESCRIPTION OF THE INVENTION

Figure 1:
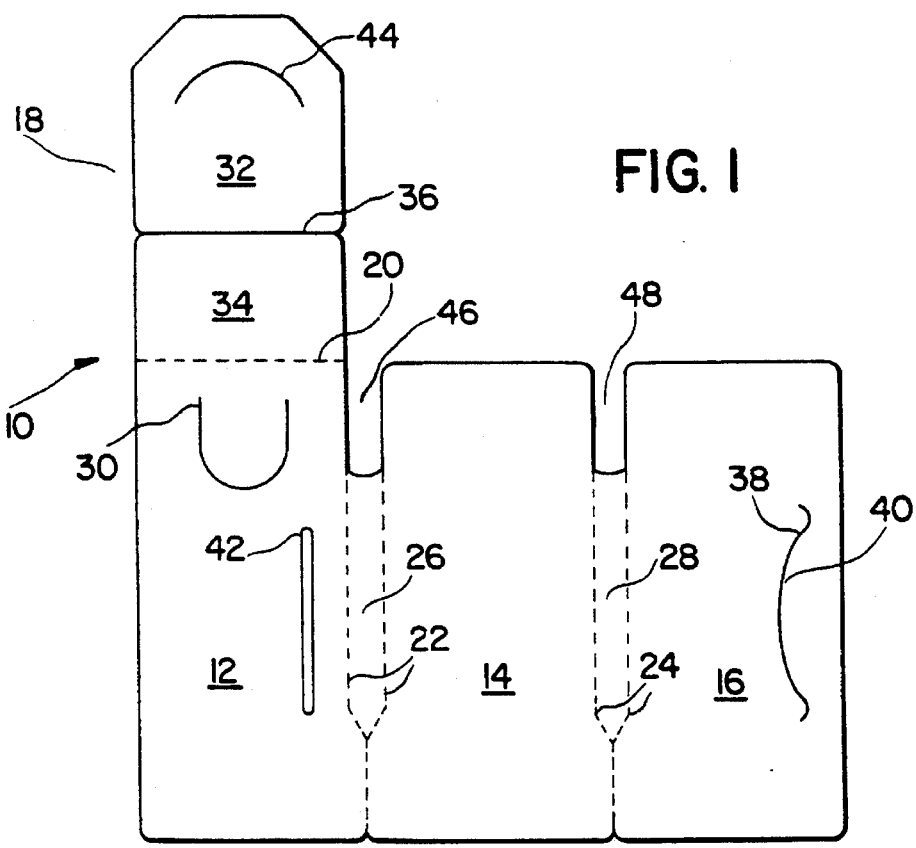
FIG. 1 is a plan view of the retainer of the present invention in the fully unfolded condition.

Referring now in specific detail to the drawings, in which like reference numerals identify similar or identical elements throughout the several views, FIG. 1 illustrates an unloaded suture reel dispenser retainer 10 in accordance with this invention. Retainer 10 is provided as a series of interconnected panels, namely reel panel 12, cover panel 14 and back panel 16. Extension panel 18 is detachably secured to upper edge 20 of reel panel 12 and possesses upper and lower sections 32 and 34, respectively. Upper edge 20 of panel 12 is slightly above the upper edges of panel 14 and 16. This feature enables upper edge 20 to be readily accessible so that extension panel 18 may be detached from retainer 10 to reveal the reel dispenser during operating procedures. Upper section 32 is foldable over lower section 34 along fold line 36 to enclose the suture reel dispenser when the dispenser is loaded in the retainer as will be described below. Retainer 10 is preferably formed from a single sheet of suitable material, e.g., stiff paper or paperboard such as 5 point to 12 point solid, TYVEK™, which is a fibrous material constructed of spun bonded polyolefin fibers, bleached sulfate board, plastics, foils, laminates, and the like, which is die cut to provide the desired configuration.

Panels 12, 16 are joined to cover panel 14 by partial double perforated lines 22, 24 (and their associated gusset sections 26, 28), respectively. Double lines 22, 24 may, in the alternative, be score lines. Gusset sections 26, 28 accommodate a limited degree of expansion of the retainer in its loaded, fully folded condition. Gusset sections 26, 28 may extend the full length of retainer 10, but preferably terminate at a point below the upper edge of the retainer thereby forming openings 46, 48. In the folded condition of retainer 10, openings 46, 48 provide easy access to the loaded suture reel dispenser. Gusset sections 26, 28 also taper in width in the lower section of the retainer 10.

Reel panel 12 possesses a U-shaped slit which defines U-shaped reel tab 30 in the upper section of the panel. Reel tab 30 can be lifted from the plane of the panel to engage select components of a suture reel dispenser to limit movement of the dispenser and to prevent its accidental removal.

Back panel 16 possesses crescent shaped tab 40 defined by arcuate slit 38. Reel panel 12 includes locking slot 42, wherein, in the folded condition of retainer 10, tab 40 of panel 16 cooperates with locking slot 42 of panel 12 to maintain the panels in a closed position. Extension panel 18 possesses locking tab 44, which engages with the upper edge of cover panel 14 in the folded condition of retainer 10 to closably secure the extension panel.

Figure 2:
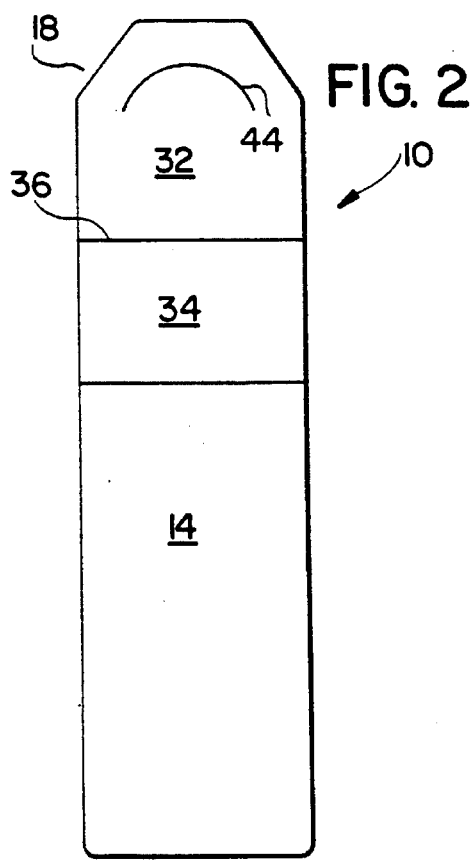
FIG. 2 is a plan view of the retainer of FIG. 1 shown in the partially folded condition.
Figure 3:
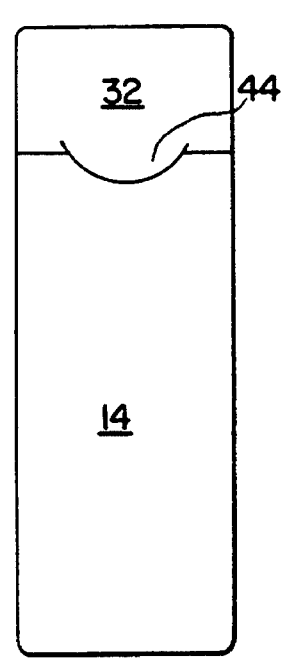
FIG. 3 is a plan view of the retainer of FIG. 1 in the fully folded condition.
Figure 4:
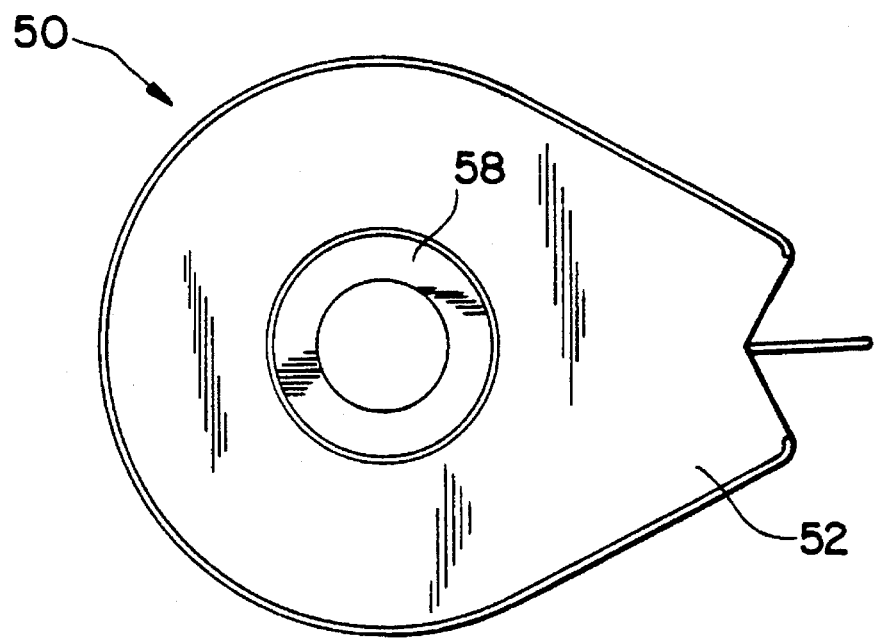
FIGS. 4 and 5 are, respectively, rear (FIG. 4) and front (FIG. 5) views of a suture reel dispenser to be loaded in the retainer of FIG. 1.
Figure 5:
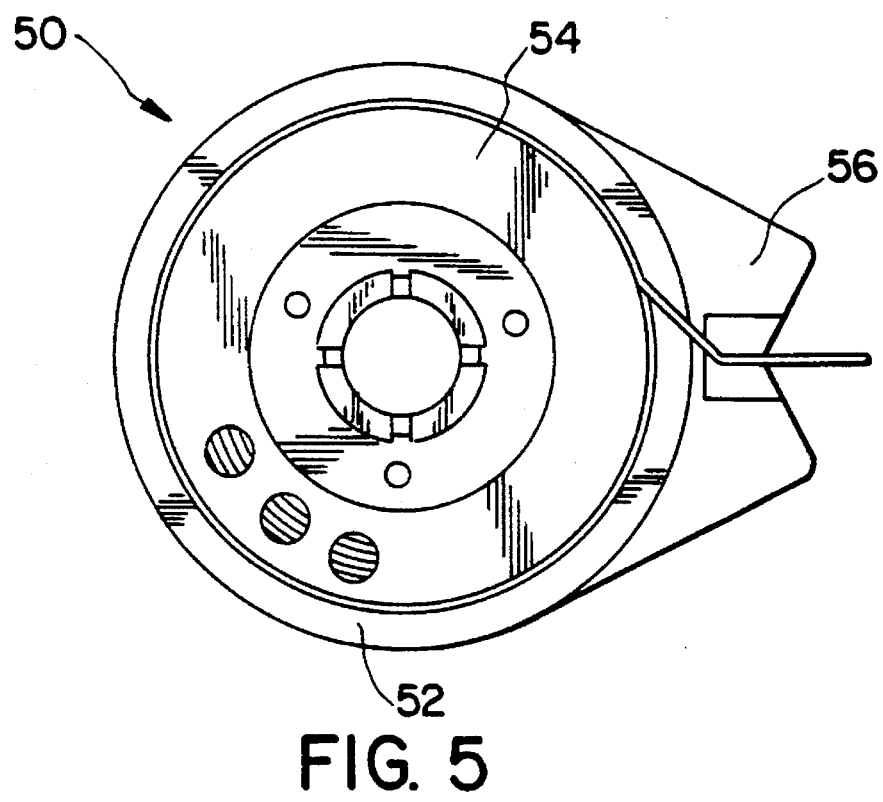
Figure 6:
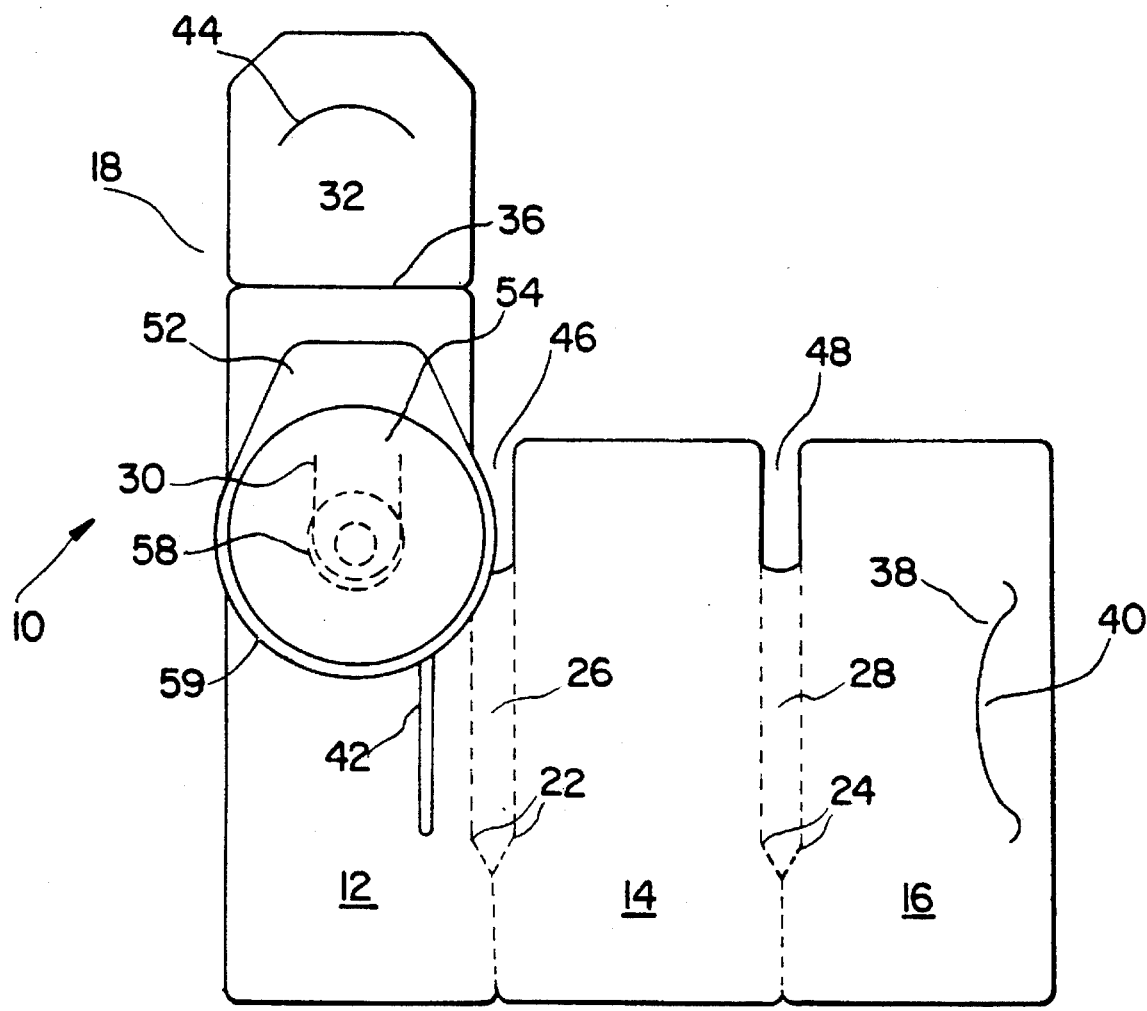
FIG. 6 is a plan view of the retainer of FIG. 1 with the suture reel dispenser of FIGS. 4 and 5 positioned on a first panel of the retainer.

The retainer 10 of FIGS. 1–3 is configured to receive a suture reel dispenser of the type illustrated in FIGS. 4 and 5. Referring to FIGS. 4 and 5 suture dispenser 50 possesses a receptacle component 52 of substantially circular configuration and an extension portion 56. The receptacle component 52 receives suture reel 54. A concentrical hub recess 58 is formed on the rear surface of the receptacle 52. Receptacle 52 may also possess a plurality of serrations 59, as seen in FIG. 6, disposed on the outer peripheral surface of the receptacle. It is clear that retainer 10 may also engage various suture reels, such as those which only provide suture reel 54 without component 52.

To load suture reel dispenser 50 into retainer 10, the retainer is first placed in its folded condition. Reel panel 12 is folded over double perforated line 22 and onto cover panel 14. Back panel 16 is then folded along double perforated line 24 and onto the rear of reel panel 12. Tab 40 of back panel 16 is positioned within locking slot 42 to secure the panels together and to form a pocket wherein the suture dispenser may be received.

Figure 7:
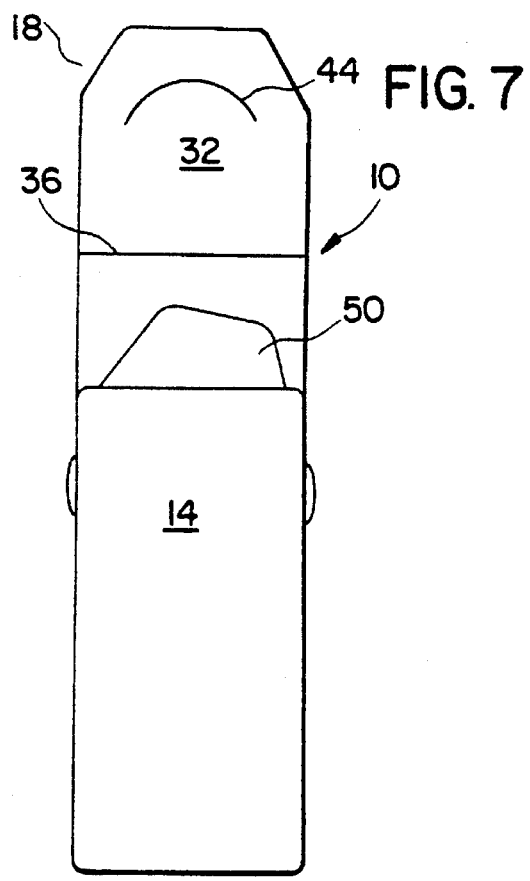
FIG. 7 is a plan view of the retainer of FIG. 1 with the suture reel dispenser of FIGS. 4 and 5 loaded therein.

Suture reel dispenser 50 is then inserted in the pocket formed by the partially folded retainer 10 preferably in the manner shown in FIG. 7. As dispenser 50 is positioned in retainer 10, U-shaped reel tab 30 projects into and engages hub recess 58 of dispenser 50. This engagement inhibits the upward movement of dispenser 50 relative to retainer 10 thereby preventing accidental removal of dispenser 50 from the retainer.

It is also possible to fold retainer 10 around a previously loaded reel dispenser 50. In accordance with this method, reel dispenser 50 is first positioned onto panel 12 as illustrated in FIG. 6, with reel tab 30 projecting into and engaging hub recess 58. Cover panel 14 and back panel 16 are then folded and secured around the reel dispenser.

As illustrated in FIG. 7, dispenser 50 is maintained in the upper portion of retainer 10. This feature of the present invention may be achieved by ensuring that the width of the pocket formed by the folded retainer is slightly smaller than the suture dispenser to be inserted. In the present embodiment, the width of retainer 10 is more narrow than the diameter of dispenser 50. Thus, as dispenser 50 is inserted into retainer 10, openings 46 and 48 allow the reel dispenser 50 to protrude outwardly while gussets 26, 28 engage the circumferential walls of the dispenser, and reel panel 12 and cover panel 14 engage the front and rear of the dispenser. Thus, a tight fit is formed around the dispenser, which thereby maintains the dispenser in the upper portion of the retainer and prevents the dispenser from entering too deeply within the pocket, to remain in a position being shown in FIG. 7. The dispenser in this position can be readily grasped by the surgeon during operating procedures, to dispense the suture material or for the complete removal of the reel from the retainer.

It is within the scope of the present invention to configure retainer 10 so that it can secure various types of suture reel dispensers. The width and depth of the pocket formed by the closed retainer may be varied to accommodate different sized reel dispensers. Furthermore, the width and depth of the pocket may be equal to or even larger than the reel dispenser to be loaded therein. Reel tab 30 may be modified to engage select components of a dispenser. For example, reel tab 30 may be made more narrow to project into the boss openings of known conventional suture reels. Reel tab 30 may also be inverted. It is also possible to provide the retainer with two reel tabs 30 and 31 on reel panel 12, as seen in FIG. 12, one reel tab configured to engage a boss opening and to prevent the upward movement of the dispenser and the second reel tab configured to support the dispenser and prevent downward movement of the dispenser into the retainer pocket.

To fully secure retainer 10 with suture reel dispenser 50 loaded therein, upper section 32 of extension panel 12 is folded over lower section 34 along perforated line 36 to enclose the suture dispenser, with locking tab 44 engaging the upper edge of cover panel 14 to completely secure the suture dispenser with the retainer, as best seen in FIG. 3.

Figure 8:
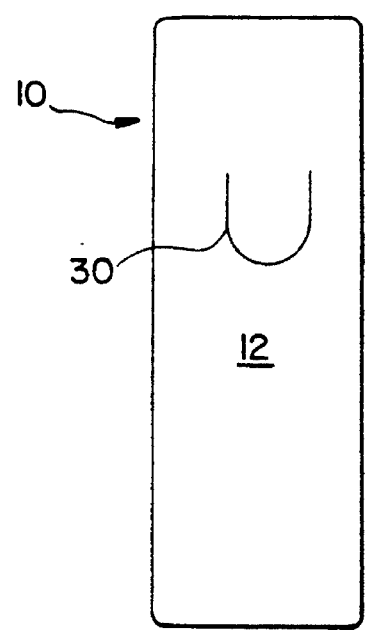
FIG. 8 is a plan view of an alternate embodiment of the retainer of FIG. 1 in the unloaded condition.
Figure 9:
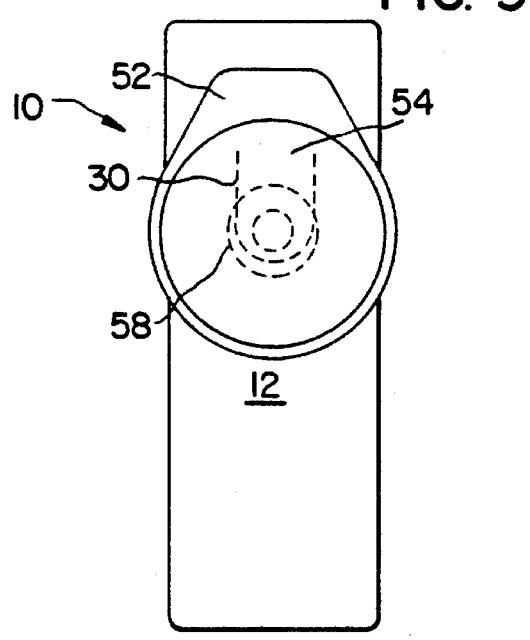
FIG. 9 is a plan view of the embodiment of the retainer of FIG. 8 with a suture reel dispenser loaded thereon.

FIG. 8 illustrates an alternate embodiment of the retainer of the present invention which provides only panel 12, having reel tab 30 thereon. After positioning a reel dispenser 50 on panel 12 by engaging a recess in the reel with reel tab 30, as seen in FIG. 9, the retainer and reel may be packaged in a so-called "breather" pouch or metal foil wrapper (not shown). Reel tab 30 would be of such a size so as to frictionally hold reel 50.

Figure 10:
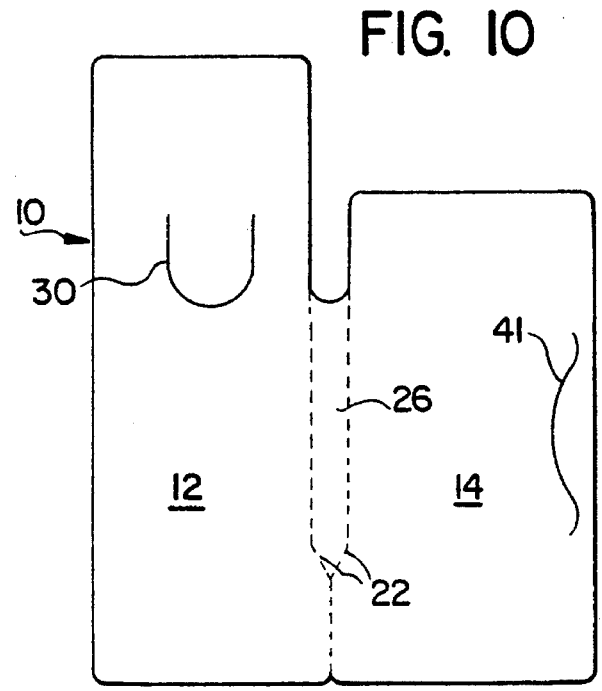
FIG. 10 is a plan view of an alternate embodiment of the retainer of FIG. 8 in the unloaded condition.

FIG. 10 illustrates an additional embodiment of the retainer 10 of FIG. 1, which is similar to the embodiment of FIG. 8 except for the provision of second panel 14. Panel 14 is joined to first panel 12 by a double perforated line 22 which forms gusset 26. As seen in FIG. 10, second panel 14 is slightly wider than panel 12 and includes means 41 for locking panel 14 over panel 12 in a folded condition. Means 41 comprises an arcuate slit 38 similar to that in FIG. 1 which engages an edge of panel 12 to hold retainer 10 in a folded condition.

FIG. 11 illustrates a further embodiment of the retainer 10 of FIG. 1, but in which the U-shaped reel tab 30 has been eliminated. The pocket formed by folding the panels about the reel dispenser 50, along with openings 46 and 48 formed by gussets 26 and 28, create a means to hold the reel dispenser in the retainer once the panels are folded and locked by the tabs 40 and 44.

Figure 13:
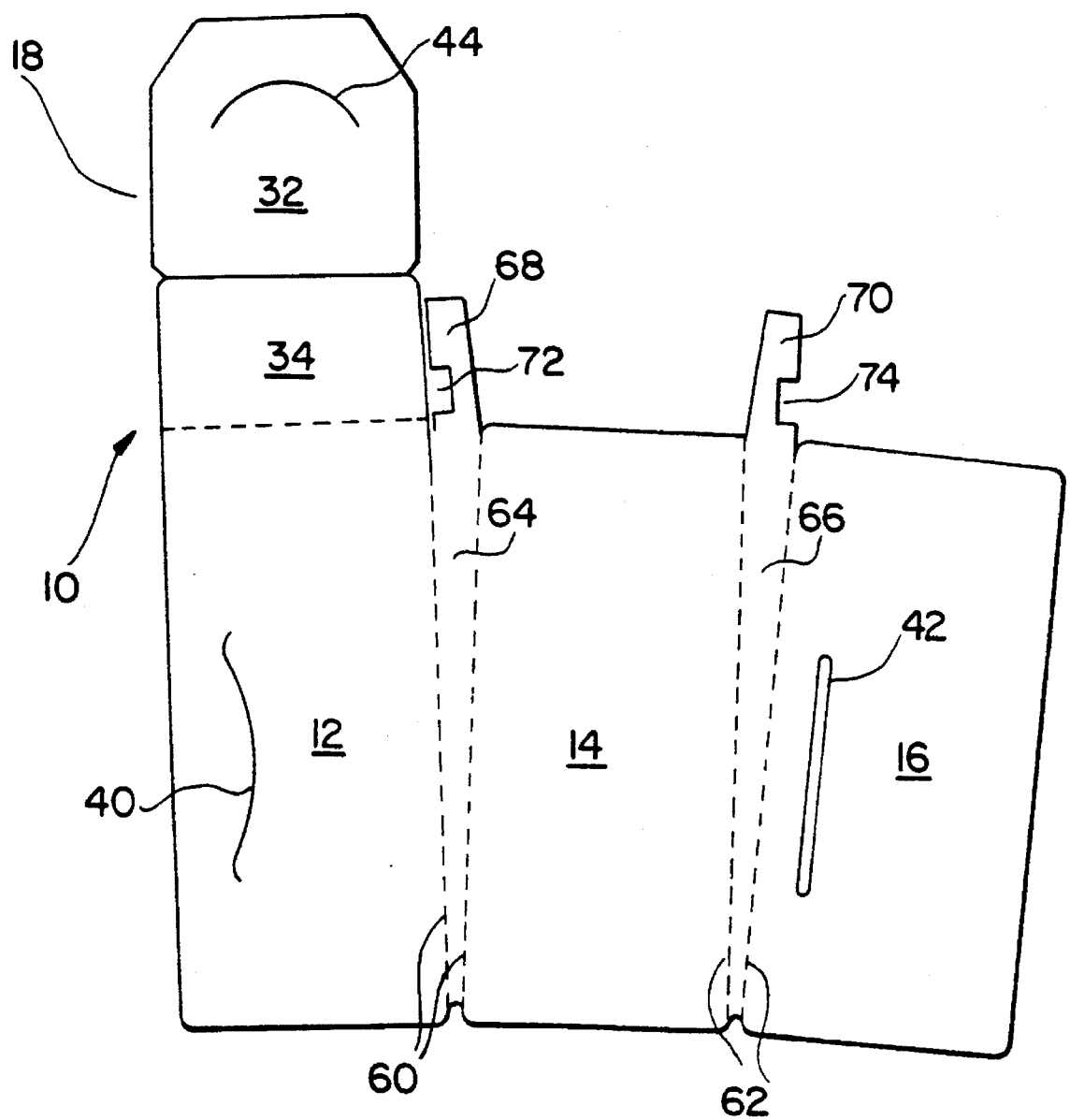
FIG. 13 is a plan view of a further alternate embodiment of the retainer of FIG. 1.
Figure 14:
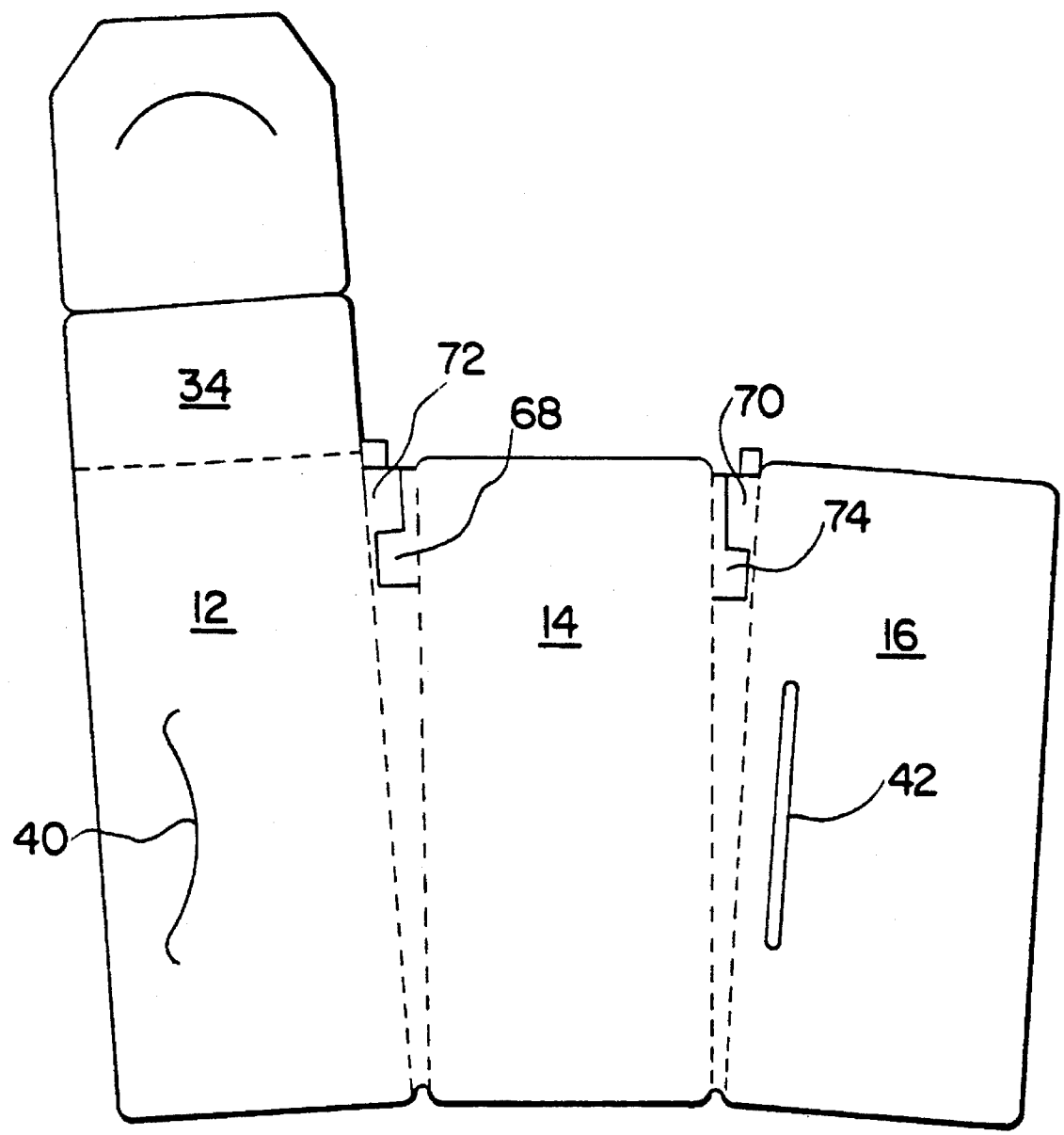
FIG. 14 is a plan view of the embodiment of FIG. illustrating the operative position of the engaging tabs.

Referring now to FIG. 13, another embodiment of the present invention is illustrated. In accordance with this embodiment, panels 12, 16 are joined to panel 14 by double perforated lines 60, 62, respectively. Double perforated lines 60 and 62, each possess two perforated lines in non-parallel arrangement, such arrangement thereby defining tapered gussets 64, 66, respectively. Engaging tabs 68, 70 are foldably connected to the upper edges of tapered gussets 64, 66, respectively, and are adapted to fold over and onto the gussets, as shown in FIG. 14, when loading the reel dispenser. Engaging tabs 68, 70 are also provided with notches 72, 74, respectively, the notches engaging select portions of the loaded reel dispenser to secure the dispenser within retainer 10 when the retainer is in the fully folded condition.

The embodiment illustrated in FIGS. 13 and 14 is configured to receive a suture reel dispenser of the type illustrated in FIGS. 4 and 5. As can be seen, crescent shaped tab 40 is now disposed on panel 12 (as opposed to reel panel 16 in the embodiment of FIG. 1) and cooperating locking slit 42 is disposed on panel 16, although these components may be positioned as in FIG. 1. Thus, in forming the pocket to receive the reel dispenser, panel 16 is first folded onto panel 14, followed by panel 12 being folded on the rear side of panel 16. As the reel dispenser is loaded within retainer 10, notches 72, 74 of engaging tabs 68, 70 engage the serrations 59 formed on the outer peripheral surface of the dispenser. This engagement inhibits the upward movement of dispenser 50 relative to retainer 10 thereby preventing accidental removal of the dispenser from the retainer. Tapered gussets 64, 66 gradually decrease the depth of the folded retainer thereby enabling the front and rear panels to engage the loaded dispenser to prevent the dispenser from entering too deeply within the formed pocket. Alternatively, the reel dispenser may be positioned on panel 14 and the panels 16 and 12 are folded over after tabs 68 and 70 are engaged.

During an operating procedure, extension panel 18 is lifted from engagement with cover panel 14 and folded back against back panel 16 to fully expose the suture reel dispenser. If necessary, extension panel 18 can be detached from the retainer. The surgeon can then readily grasp and remove the suture reel dispenser, or dispense the suture directly from the reel within the retainer.

The retainer of the present invention effectively maintains a suture reel dispenser during storage while also permitting ready access to, and removal of, the suture dispenser during operating room procedures. The retainer can be packaged within a foil package or directly in a so-called "breather pouch"(not shown).

The above embodiment has been described only as examples of the present invention and other modifications and embodiments are contemplated within the spirit and scope of the present invention as defined by the following claims.

What is claimed is:

1. A retainer for a suture reel dispenser, comprising a first panel member, a second panel member foldably connected to said first panel member along a double perforated line extending substantially the entire lengths of said first and second panel members, a third panel member foldably connected to said second panel member along a double perforated line extending substantially the entire lengths of said second and third panel members, each said double perforated line being in non-parallel arrangement to form tapered gussets between said panel members, said first, second and third panel members foldable onto each other to form a pocket for receiving at least a portion of a suture reel dispenser, said pocket having a depth defined by said tapered gussets and wherein the depth of said pocket gradually decreases in dimension from an upper portion of said pocket to a lower portion of said pocket to facilitate securement of the suture reel dispenser therein.

2. The retainer according to claim 1, further comprising an extension panel foldably connected to an upper edge of said first panel member, said extension panel being foldable to engage one of said second and third panel members to retain said extension panel in a folded condition.

3. The retainer according to claim 2, wherein said extension panel comprises an upper section and a lower section, said upper section being foldable along a perforated line over said lower section and having a locking tab which engages an upper edge of one of said second and third panel members.

4. The retainer according to claim 1, wherein a reel engaging tab is foldably connected to an upper edge of each of said gussets, said reel engaging tabs foldable within said pocket such that upon insertion of a suture reel dispenser at least partially within said pocket said reel engaging tabs engage the suture reel dispenser to assist in retention of the suture reel dispenser therein.

5. The retainer according to claim 1, wherein a crescent shaped opening is provided in said first panel member and a slit is provided in said third panel member, said opening and said slit cooperating with each other when said retainer is fully folded to provide a locking mechanism to secure said retainer in a closed position.

6. The retainer according to claim 1 further comprising a suture reel dispenser at least partially disposed within said pocket, said suture reel dispenser including a suture reel having a length of suture wound thereon.

7. The suture reel retainer package according to claim 6, wherein said pocket defined by said folded panel members is dimensioned to frictionally engage said suture reel dispenser positioned therein.

8. In combination, a suture reel dispenser and a retainer for said suture reel dispenser, said suture reel dispenser including a suture reel having a length of suture thread wound thereon, said retainer comprising a plurality of panel members foldably connected to each other along double perforated lines and foldable onto each other along said double perforated lines to form a pocket for reception of said suture reel dispenser, each said double perforated line defining a gusset between adjacent panel members, said pocket having a width defined by the width of said panel members and a depth defined by the width of said gussets, said pocket being dimensioned such that said suture reel dispenser is secured in a fixed position at least partially within said retainer by frictional engagement of said reel dispenser with said panel members and with said gussets.

9. The combination of claim 8, wherein each said double perforated line is in non-parallel arrangement, thereby defining tapered gussets.

10. The combination of claim 8, further comprising an extension panel foldably connected to an upper edge of one of said panel members and being foldable over to at least partially enclose said reel dispenser within said retainer.

11. The combination of claim 8, wherein said reel dispenser is retained within said retainer such that at least a portion of said reel dispenser is disposed beyond an upper edge of at least one of said panel members.

12. The combination of claim 11, wherein an extension panel is foldably connected to an upper edge of one of said panel members, said extension panel being foldable to at least partially enclose said reel dispenser.

13. In combination, a suture reel dispenser including a suture reel having suture thread wound thereon and a retainer for said suture reel dispenser, said retainer comprising a plurality of panel members foldably connected to each other along double perforated lines, each said double perforated lines defining a gusset between adjacent panel members, each said gusset having a reel engaging tab foldably connected to an upper edge thereof, each said reel engaging tab having an end portion for engaging said reel dispenser to assist in retaining said reel dispenser in a fixed position at least partially within said retainer.

14. The combination of claim 13, wherein said suture reel dispenser further includes a receptacle component and wherein said suture reel is disposed within said receptacle component, said receptacle component having serrations formed on an outer peripheral surface thereof, said end portions of said reel engaging tabs engageable with said serrations of said reel dispenser to retain said reel dispenser within said retainer.

15. The combination of claim 13, further comprising an extension panel foldably connected to an upper edge of one of said panel members and being foldable to at least partially enclose said reel dispenser within said retainer.

16. The combination of claim 13 wherein each said reel engaging tab is foldable toward its respective gusset such that said end portions of each said reel engaging tab engage a peripheral surface defined by said reel dispenser to assist in retaining said reel dispenser within said retainer.

17. The combination according to claim 16, wherein said engaging tabs each have a notch formed therein, said notches engaging serrations formed on said peripheral surface of said reel dispenser.

18. In combination, a suture reel dispenser and a retainer for said suture reel dispenser, said retainer comprising a plurality of panel members foldably connected to each other along double perforated lines, each said double perforated lines defining a gusset between adjacent panel members, each said gusset having a reel engaging tab foldably connected to an upper edge thereof, each said reel engaging tab having a notch dimensioned and positioned to engage said reel dispenser when said reel engaging tabs are folded toward said gussets to assist in retaining said reel dispenser in a fixed position within said retainer.

19. The combination of claim 18, wherein said notches engage serrations formed on an outer surface of said reel dispenser.

20. In combination, a suture reel dispenser and a retainer for said reel dispenser, said reel dispenser comprising a cylindrically shaped receptacle adapted to rotatably receive a suture reel on a first side and having a recess formed on a second side, said reel having a length of suture material wound thereon;

said retainer comprising a first panel member, a second panel member foldably connected to the first panel member by a double perforated line, a third panel member foldably connected to the second panel member by a double perforated line, said double perforated lines forming gussets between said panel members, said first, second and third panel members being foldable onto each other to form a pocket to receive said reel dispenser so that said reel dispenser is at least partially exposed at said upper edge, an extension panel foldably connected to an upper edge of said first panel member, said extension panel being foldable over the suture reel dispenser, and an engaging tab foldably connected to each of said gussets for engaging a peripheral surface of said reel dispenser;

wherein the width of said pocket formed by said retainer in the folded condition is smaller than the diameter of the suture reel dispenser to thereby limit entry of the suture reel dispenser into said retainer and maintain the dispenser in a partially exposed position.

21. The combination of claim 20, wherein said suture reel further comprises serrations formed on an outer peripheral surface.

22. A retainer for a suture reel dispenser comprising a row of panel members foldably connected to each other along double perforated lines and foldable onto each other to form a pocket to at least partially accommodate a suture reel dispenser, said double perforated lines forming gussets between adjacent panel members, each said gusset having a reel engaging tab foldably connected to an upper edge thereof, each said reel engaging tab foldable within said pocket and defining engaging portions such that upon at least partial insertion of a suture reel dispenser in said pocket said engaging portions of said reel engaging tabs engage the suture reel dispenser to assist in at least partially retaining the suture reel dispenser therein.

23. A retainer for a suture reel dispenser comprising a row of panel members foldably connected to each other along double perforated lines and foldable onto each other to form a pocket to at least partially accommodate a suture reel dispenser, said double perforated lines forming gussets between adjacent panel members, each said gusset having a reel engaging tab foldably connected to the upper edge thereof, each said reel engaging tab foldable within said pocket and having a notch formed therein dimensioned and configured to engage a suture reel dispenser upon insertion thereof into said pocket to facilitate retention of the suture reel dispenser therein.

24. A suture reel dispenser package, comprising:

suture reel dispenser means for retaining and dispensing suture;

a plurality of panel members foldably connected to each other and arranged to fold onto each other to form a pocket for at least partial reception of the suture reel dispenser means; and means associated with the panel members for retaining the suture reel dispenser means in the pocket in a position wherein at least a portion of the suture reel dispenser means extends beyond an upper edge of one of the panel members.

25. In combination, a suture dispenser and a retainer for said suture dispenser, said retainer comprising a plurality of panel members foldably connected to each other along double perforated lines, each said double perforated lines defining a gusset between adjacent panel members, each said gusset having an engaging tab foldably connected to an upper edge thereof, each said engaging tab having a notch dimensioned and positioned to engage said dispenser when said engaging tabs are folded toward said gussets to assist in retaining said dispenser in a fixed position within said retainer.

* * * * *